United States Patent
Huang

(10) Patent No.: US 10,948,477 B2
(45) Date of Patent: Mar. 16, 2021

(54) MOISTUREPROOF CONTAINER STRUCTURE FOR ACCOMMODATING BIOCHEMICAL TEST STRIP

(71) Applicant: Liao-Chuan Huang, Taoyuan (TW)

(72) Inventor: Liao-Chuan Huang, Taoyuan (TW)

( * ) Notice: Subject to any disclaimer, the term of this patent is extended or adjusted under 35 U.S.C. 154(b) by 0 days.

(21) Appl. No.: 16/814,004

(22) Filed: Mar. 10, 2020

(65) Prior Publication Data

US 2020/0217834 A1    Jul. 9, 2020

Related U.S. Application Data

(62) Division of application No. 16/128,767, filed on Sep. 12, 2018, now Pat. No. 10,677,777.

(30) Foreign Application Priority Data

Oct. 31, 2017 (TW) .............................. 106216152 U
Oct. 31, 2017 (TW) .............................. 106216155 U

(51) Int. Cl.
| G01N 33/487 | (2006.01) |
| B65D 81/26 | (2006.01) |
| B05D 5/00 | (2006.01) |
| B05D 1/18 | (2006.01) |
| B05D 1/02 | (2006.01) |

(52) U.S. Cl.
CPC ......... *G01N 33/48778* (2013.01); *B05D 1/02* (2013.01); *B05D 1/18* (2013.01); *B05D 5/00* (2013.01); *B65D 81/264* (2013.01)

(58) Field of Classification Search
CPC ................................................ G01N 33/48778

USPC ............................................ 428/98; 206/204
See application file for complete search history.

(56) References Cited

U.S. PATENT DOCUMENTS

| 4,383,376 A | 5/1983 | Numamoto et al. |
| 2011/0127175 A1* | 6/2011 | Chan .................... B65D 25/101 |
| | | 206/204 |

FOREIGN PATENT DOCUMENTS

| CN | 101175632 A | 5/2008 |
| CN | 201381045 Y | 1/2010 |
| CN | 201784933 U | 4/2011 |
| CN | 203155245 U | 8/2013 |
| CN | 203383104 U | 1/2014 |
| CN | 204957361 U | 1/2016 |
| CN | 107530617 A | 1/2018 |
| CN | 107686578 A | 2/2018 |

OTHER PUBLICATIONS

Search Report for Corresponding CN Application 201810438099.1 dated Oct. 26, 2020.

* cited by examiner

*Primary Examiner* — Brent T O'Hern
(74) *Attorney, Agent, or Firm* — Rosenberg, Klein & Lee

(57) ABSTRACT

A moistureproof container for accommodating a biochemical test strip. The moistureproof container includes a moistureproof unit disposed in the container body which houses the biochemical test strip. The moistureproof unit is formed of a hydrophilic polymer material on a surface of a carrier. The moistureproof unit is disposed in the container body which houses the biochemical test strip and absorbs the moisture in the container body.

11 Claims, 12 Drawing Sheets

MOISTUREPROOF CONTAINER STRUCTURE FOR ACCOMMODATING BIOCHEMICAL TEST STRIP

CROSS-REFERENCE TO RELATED APPLICATION

This application is a divisional of application U.S. Ser. No. 16/128,767, filed 12 Sep. 2018, now U.S. Pat. No. 10,677,777, and claims under 35 USC § 119(a) the benefit of Taiwanese Application NO. 106216155, filed on Oct. 31, 2017 and Taiwanese Application NO. 106216152, filed on Oct. 31, 2017, the entire disclosure of which is incorporated herein by reference.

BACKGROUND

1. Technical Field

The present disclosure relates to a moistureproof patch, in particular, to a moistureproof unit having the moistureproof patch, a moistureproof container structure with a great moistureproof effect for accommodating at least one biochemical test strip.

2. Description of Related Art

Conventional biochemical test strips may usually be disposed in containers, wherein a center of each container may have room, a top of the container may have a cover body, and the biochemical test strip is disposed in the room of the container, such that the biochemical test strip is isolated from the outside. To increase the moistureproof effect, moistureproof grains can be filled in the cover body for generating a moisture absorption effect. Thus, the biochemical test strip is prevented from be failed due to the moisture.

However, the moistureproof grains are disposed in the cover body, not only the moisture under the room is not absorbed efficiently to cause the poor moistureproof effect, but also the biochemical test strip is not easily taken out. Thus, the moistureproof effect is poor, and under the long-time usage, the biochemical test strip is still damped to affect the whole test result.

SUMMARY

An objective of the present disclosure is to provide a method for manufacturing a moistureproof unit and a moistureproof container structure for accommodating at least one biochemical test strip, wherein the moistureproof unit is configured to absorb moisture, and the semicircular or hemispherical water absorption unit can generate a large absorption area to enhance the moisture absorption effect, therefore reducing the precision requirement of the thermocompression part, and decreasing the cost of the thermocompression process. Since the strength of the thermocompression is decreased, the user will use less force when tearing off. In addition, the moistureproof unit can efficiently absorb the moisture being induced into the packaging body, so as to prevent the biochemical test strip being failed.

One main objective of the present disclosure is to provide a method for manufacturing a moistureproof unit and a moistureproof container structure for accommodating at least one biochemical test strip, wherein the moistureproof unit is fully distributed on the container body and the cover body to increase the moisture absorption area, thus providing a great moisture absorption effect. The water absorption unit can generate a large absorption area to enhance the moisture absorption effect, such that the whole moisture in the moistureproof container structure for accommodating the biochemical test strip is absorbed to prevent the non-uniform absorption problem.

The present disclosure provides a method for manufacturing a moistureproof unit, at least comprising: preparing a carrier: a shape the carrier is a sheet; and coating a moistureproof layer: prepared hydrophilic polymer material is uniformly distributed on the carrier, and a plurality of water absorption units being semicircular are formed on a surface of the carrier.

In accordance to the above features, wherein coating the moistureproof layer is processed by a spraying manner.

In accordance to the above features, wherein coating the moistureproof layer is processed by a dispensing manner.

In accordance to the above features, wherein a height of the water absorption unit is 0.2 mm through 0.6 mm, preferably 0.25 mm through 0.5 mm, and optimally 0.3 mm.

In accordance to the above features, wherein a diameter of the water absorption unit is 0.3 mm through 1.2 mm, preferably 0.5 mm through 0.9 mm, and optimally 0.6 mm.

In accordance to the above features, wherein a distance between the two neighboring water absorption units is between 0.17 mm through 0.57 mm.

In accordance to the above features, wherein a grain weight of the water absorption unit is 0.011 g through 0.013 g.

In accordance to the above features, wherein material of the water absorption unit is light-hardening resin with a viscosity being 16000 through 24000 (25° C., S14 10RPM, CPS), a specific weight being 1.1 (25° C.) and a PH value being 1.21, wherein each of the water absorption units formed by using a dispensation of a piezoelectric nozzle has a height being 0.3 mm, a diameter being 0.6 mm and a grain weight being 0.012 g, and a distance between the two neighboring water absorption units is 0.37 mm.

The present disclosure further provides a moistureproof container structure for accommodating at least one biochemical test strip, at least comprising: a moistureproof unit, being manufactured to have the above structure; and a container body having a room, wherein the moistureproof unit is fixed in the room.

In accordance to the above features, wherein one side of the room of the container body has an opening, a periphery of the room has a side wall surrounding the periphery of the room, and a bottom of the room has a bottom wall, the biochemical test strip is accommodated in an interior of the room, wherein a top of the container body further has a cover body being configured to cover the opening.

In accordance to the above features, wherein another side of the moistureproof layer of the moistureproof unit has an adhesion layer being adhered to the side wall of the room.

In accordance to the above features, wherein a side the moistureproof unit is coated with an adhesion layer.

In accordance to the above features, wherein the moistureproof unit is spirally adhered to the cover body via the side of the moistureproof unit.

In accordance to the above features, wherein one side of the cover body has a connection rib being coupled to the container body.

In accordance to the above features, wherein the container body is formed by jointing at least one packaging sheet, a periphery of the packaging sheet has a thermocompression part surrounding the periphery of the packaging sheet, the room being closed is formed between the packaging sheet and the thermocompression part, and the biochemical test strip is accommodated in an interior of the room; wherein a side of the carrier has an adhesion layer being adhered to the packaging sheet, another side of the carrier has the moistureproof layer, and the moistureproof unit is disposed in the room.

In accordance to the above features, wherein the biochemical test strip is selected from one of a blood glucose test strip, a uric acid test strip, a urine test strip, a lactic acid test strip and a cholesterol test strip.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Figure 1:
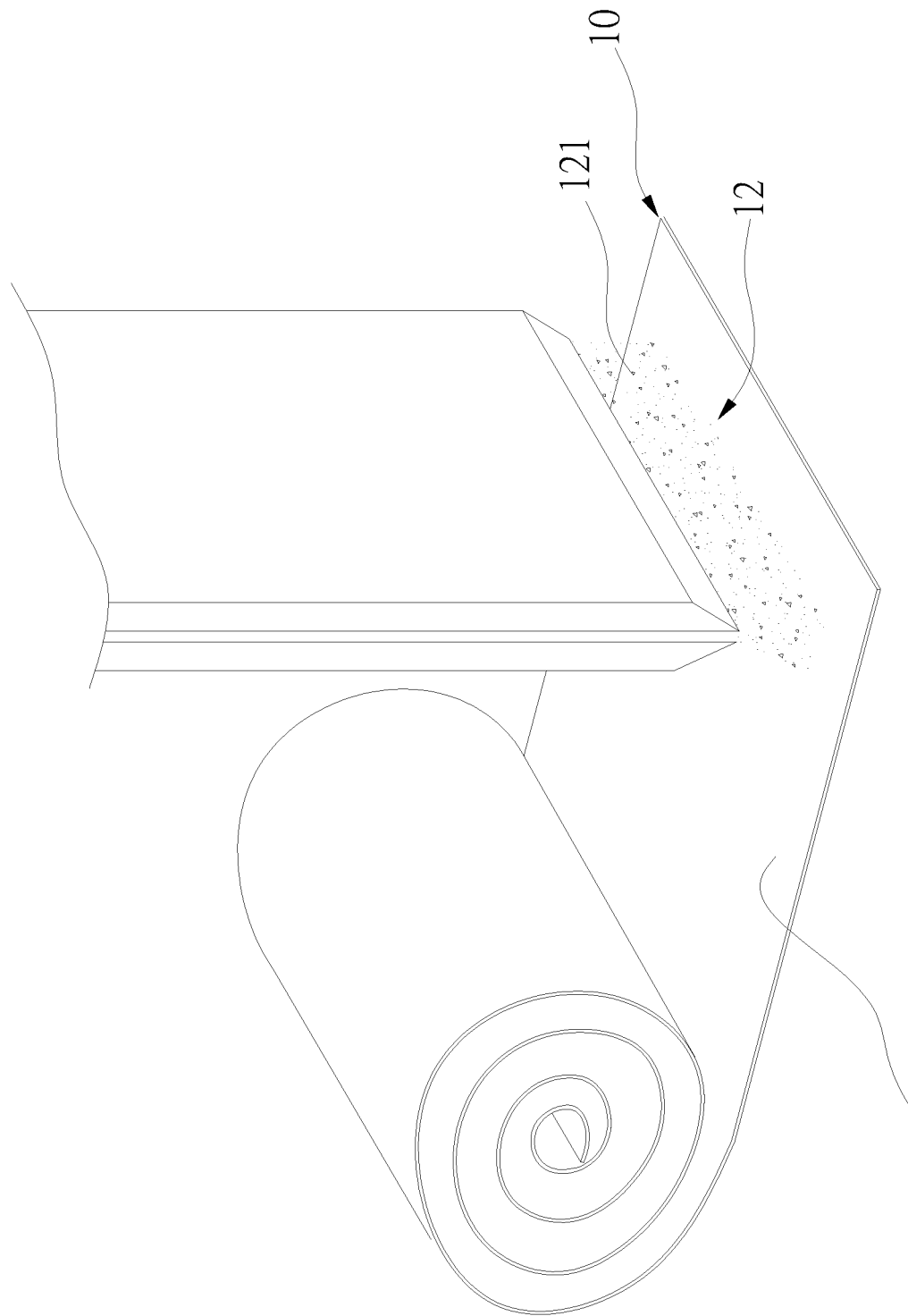
FIG. 1 is a schematic diagram showing a first method for manufacturing a moistureproof unit of the present disclosure.
Figure 2:
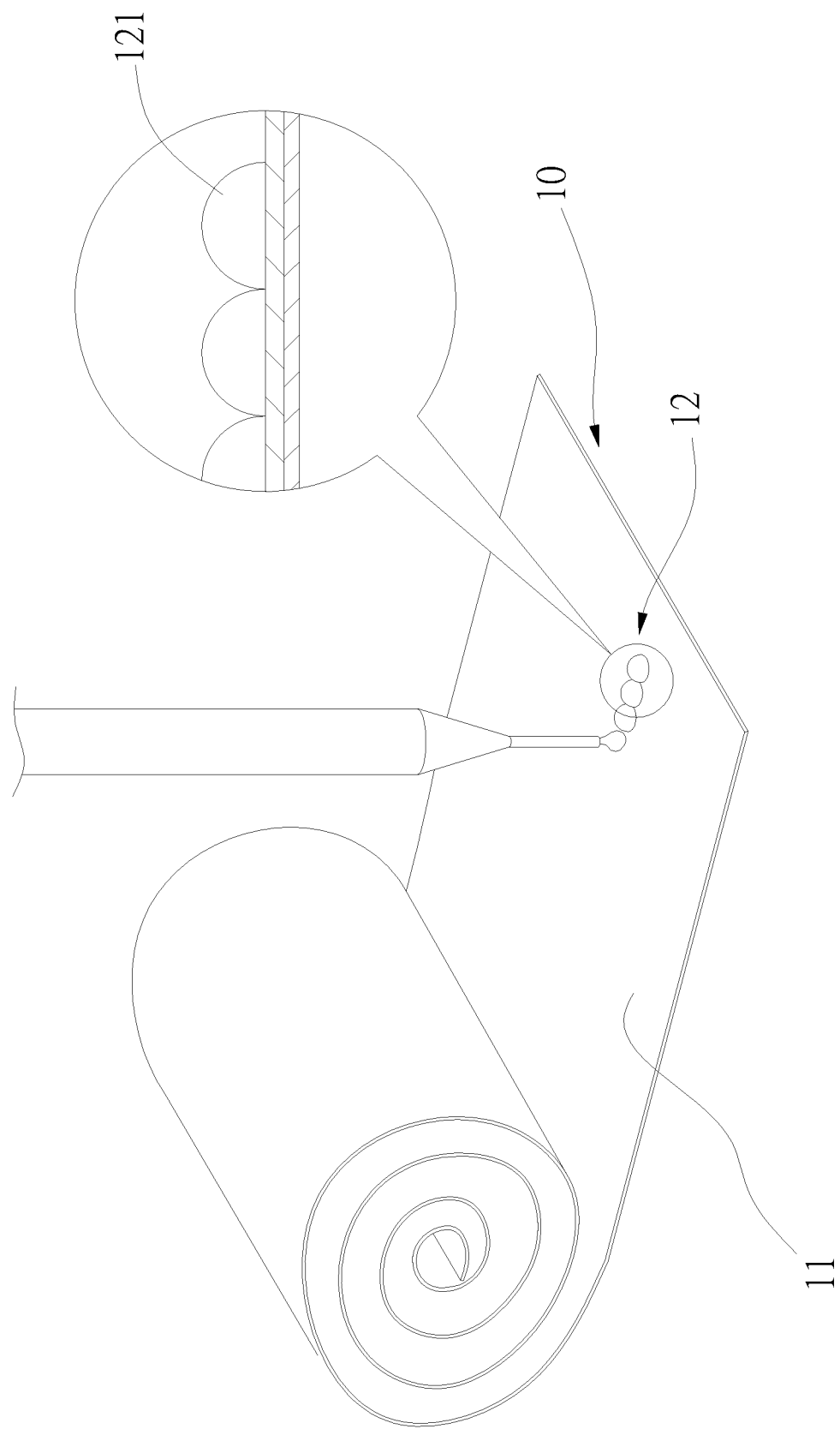
FIG. 2 is a schematic diagram showing a second method for manufacturing a moistureproof unit of the present disclosure.
Figure 3:
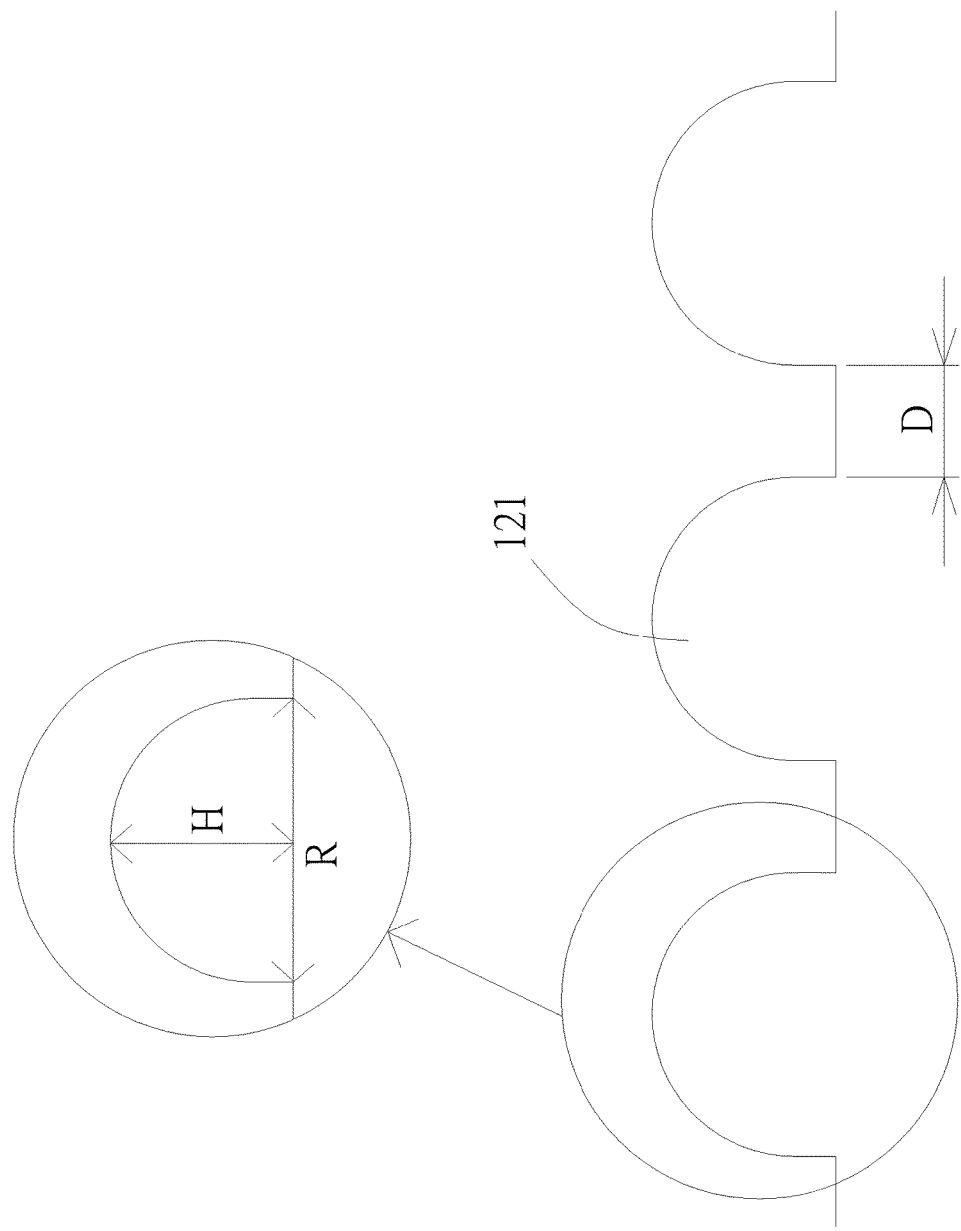
FIG. 3 is a first schematic diagram showing a water absorption unit of the present disclosure.

Referring to FIG. 1 and FIG. 2, the present disclosure provides a method for manufacturing a moistureproof unit, at least comprising: preparing a carrier 11: a shape the carrier 11 is a sheet; and coating a moistureproof layer 12: prepared hydrophilic polymer material is uniformly distributed on the carrier 11, and a plurality of water absorption units 121 being semicircular are formed on a surface of the carrier 11. Specifically, coating the moistureproof layer 12 can be processed by a spraying manner as shown in FIG. 1, and the water absorption units 121 of the moistureproof layer 12 can be irregularly distributed and coated on the carrier 11; or alternatively, as shown in FIG. 2, coating the moistureproof layer 12 can be processed by a dispensing manner, and in accordance to the design, the water absorption unit 121 is regularly and uniformly coated on the carrier 11.

Figure 4:
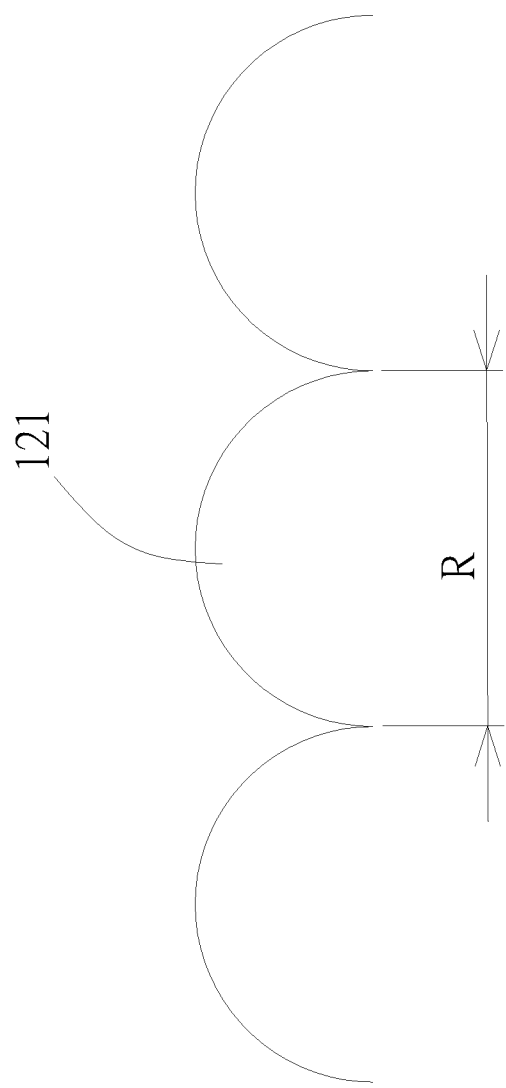
FIG. 4 is a second schematic diagram showing a water absorption unit of the present disclosure.
Figure 5:
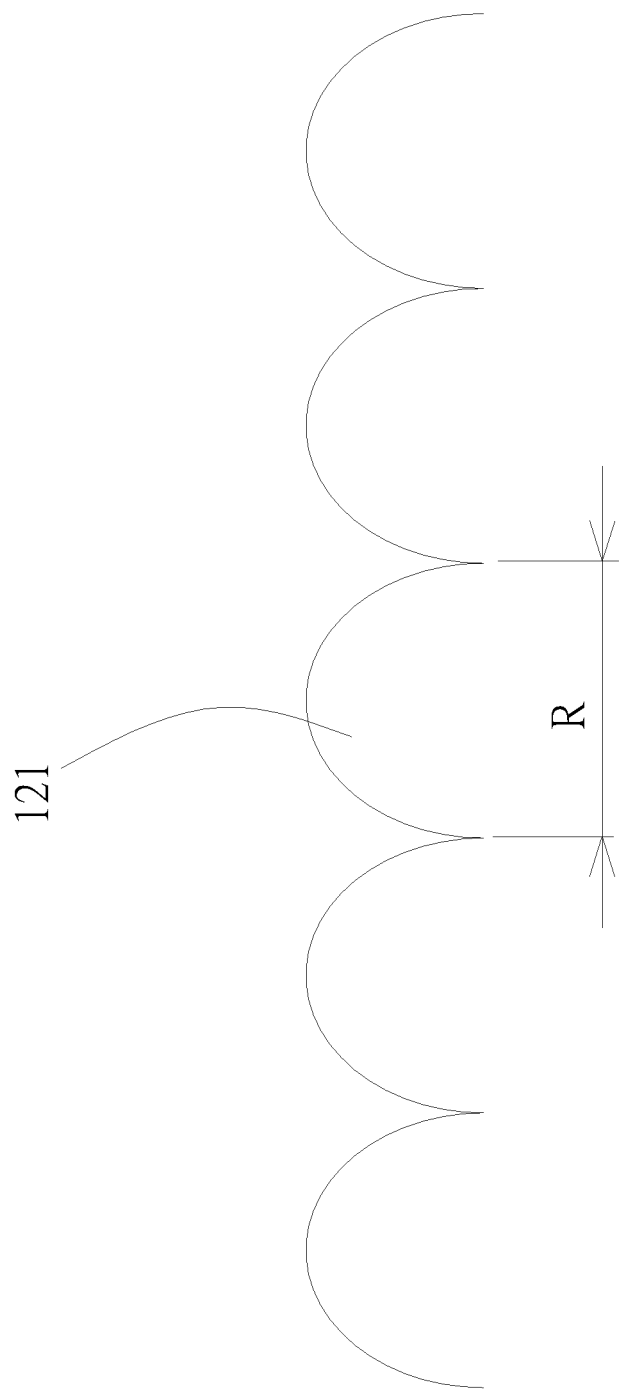
FIG. 5 is a third schematic diagram showing a water absorption unit of the present disclosure.
Figure 6:
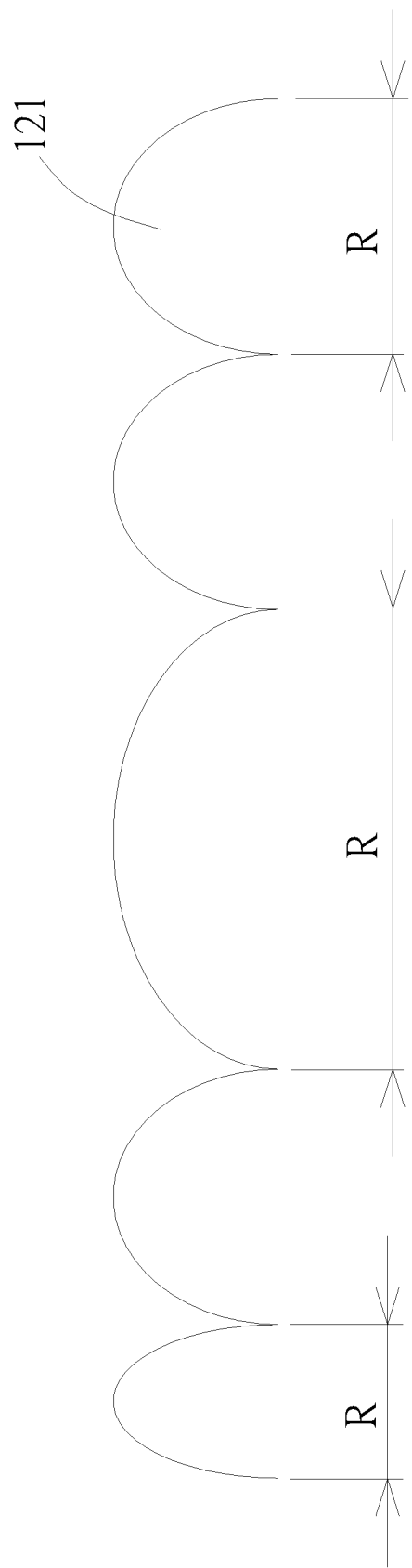
FIG. 6 is a fourth schematic diagram showing a water absorption unit of the present disclosure.
Figure 7:
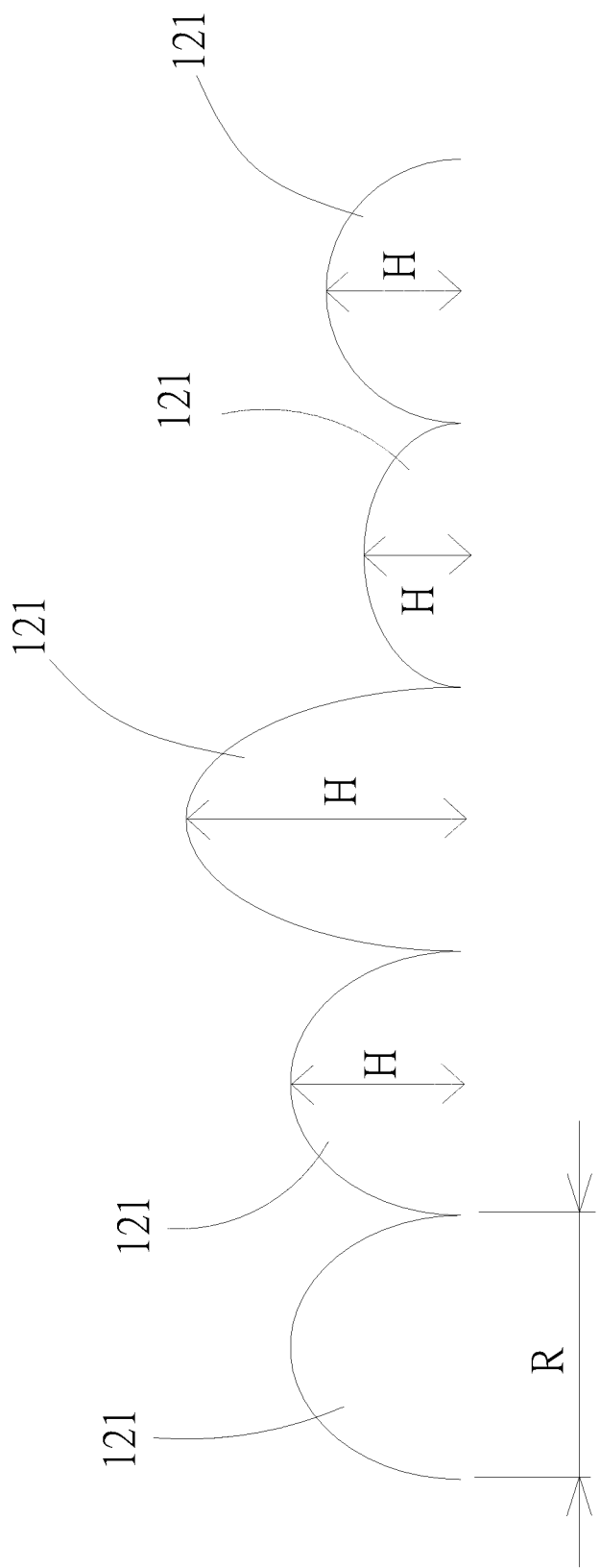
FIG. 7 is a fifth schematic diagram showing a water absorption unit of the present disclosure.

Referring to FIG. 3 through FIG. 7, a height H of the water absorption unit 121 is 0.2 mm through 0.6 mm, preferably 0.25 mm through 0.5 mm, and optimally 0.3 mm; a diameter R of the water absorption unit 121 is 0.3 mm through 1.2 mm, preferably 0.5 mm through 0.9 mm, and optimally 0.6 mm; a distance D between the two neighboring water absorption units 121 is between 0.17 mm through 0.57 mm; and a grain weight of the water absorption unit 121 is 0.011 g through 0.013 g. In the embodiment, material of the water absorption unit is light-hardening resin with a viscosity being 16000 through 24000 (25° C., S14 10RPM, CPS), a specific weight being 1.1(25° C.) and a PH value being 1.21, wherein each of the water absorption units 121 formed by using a dispensation of a piezoelectric nozzle has a height H being 0.3 mm, a diameter R being 0.6 mm and a grain weight being 0.012 g, and a distance D between the two neighboring water absorption units 121 is 0.37 mm. In addition, further referring to FIG. 3, the distance D is formed between the two neighboring water absorption units 121, and the distance D is 0.17 mm through 0.57 mm. The diameters R of the water absorption units 121 shown in FIG. 4 and FIG. 5 are the same one, and the heights H of the water absorption units 121 shown in FIG. 4 and FIG. 5 are the same one. As shown in FIG. 6, the water absorption units 121 may be formed to have different diameters R. As shown in FIG. 7, the water absorption units 121 may be formed to have different heights H. That is, the water absorption units 121 may be formed to have different parameters according to actual requirements.

Figure 8:
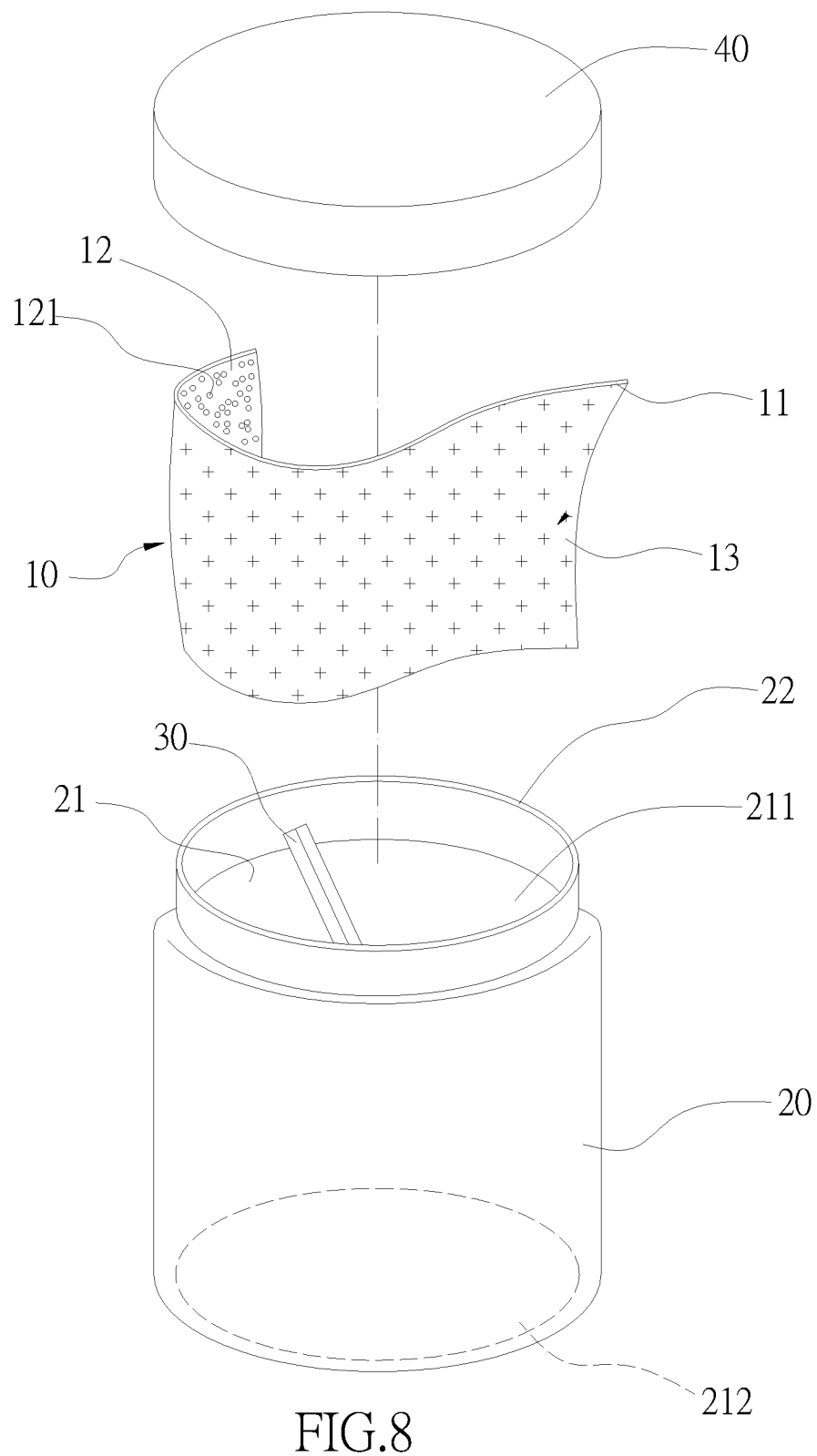
FIG. 8 is an explosive diagram showing a moistureproof patch being applied to a container of the present disclosure.
Figure 9:
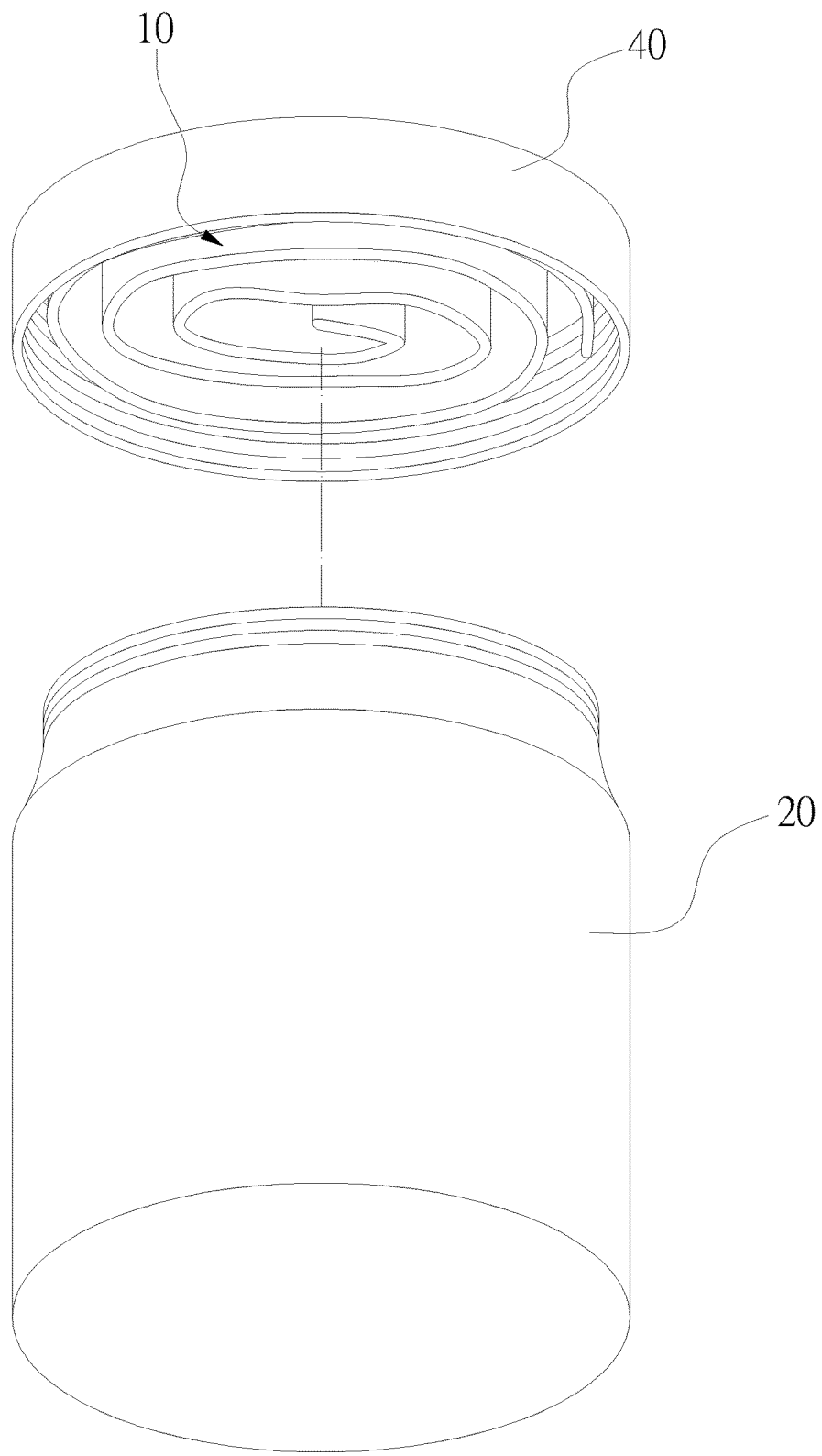
FIG. 9 is an explosive diagram showing a moistureproof patch being applied to a cover body of a container of the present disclosure.
Figure 10:
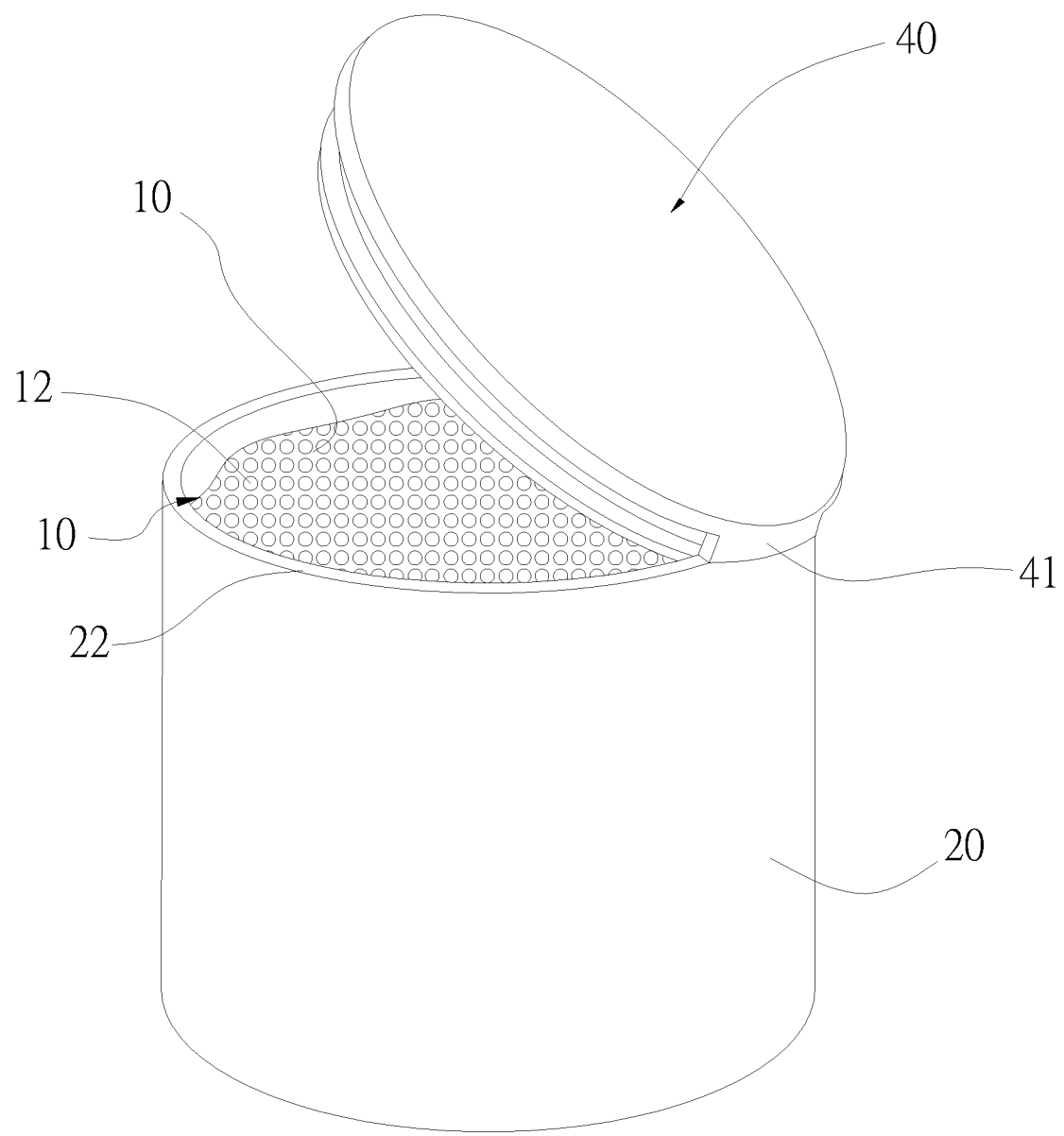
FIG. 10 is a three dimensional diagram showing a moistureproof patch being applied to a clamshell container of the present disclosure.

Referring to FIG. 8 through FIG. 10, when the moistureproof units 10 are used, a container body 20 may have a room 21, wherein one side of the room 21 has an opening 22, a periphery of the room 21 has a side wall 211 surrounding the periphery of the room 21, and a bottom of the room 21 has a bottom wall 212, and the biochemical test strip 30 is accommodated in an interior of the room 21. Referring to FIG. 8, the biochemical test strip is selected from one of a blood glucose test strip, a uric acid test strip, a urine test strip, a lactic acid test strip and a cholesterol test strip.

The cover body 40 is configured to cover the opening 22, so as to make the room 21 be closed. The moistureproof unit 10 at least comprises the carrier 11, wherein a side of the carrier 11 has the moistureproof layer 12, and another side of the carrier 11 has an adhesion layer 13. The moistureproof layer 12 has the semicircular water absorption units 121 coated and disposed on the carrier 11. The moistureproof unit 10 is configured to make the adhesion layer 13 be adhered to the side wall 211 of the room 21. As shown in FIG. 7, the adhesion layer 13 is adhered to the whole or partial periphery of the side wall 211, such that the moistureproof layer 12 is disposed on the surface of the room 21. In addition, the adhesion layer 13 of the moistureproof unit 10 is disposed on the side of the moistureproof unit 10, and as shown in FIG. 9, the moistureproof unit 10 is rolled to have a spiral shape. The moistureproof unit 10 is adhered to the bottom of the cover body 40, and when the cover body 40 covers the container body 20, the moistureproof unit 10 is floated in the room 21. Furthermore, referring to FIG. 10, the cover body 40 may also have a connection rib 41 coupled to the container body 20, so as to prevent the cover body 40 from being lost.

Figure 11:
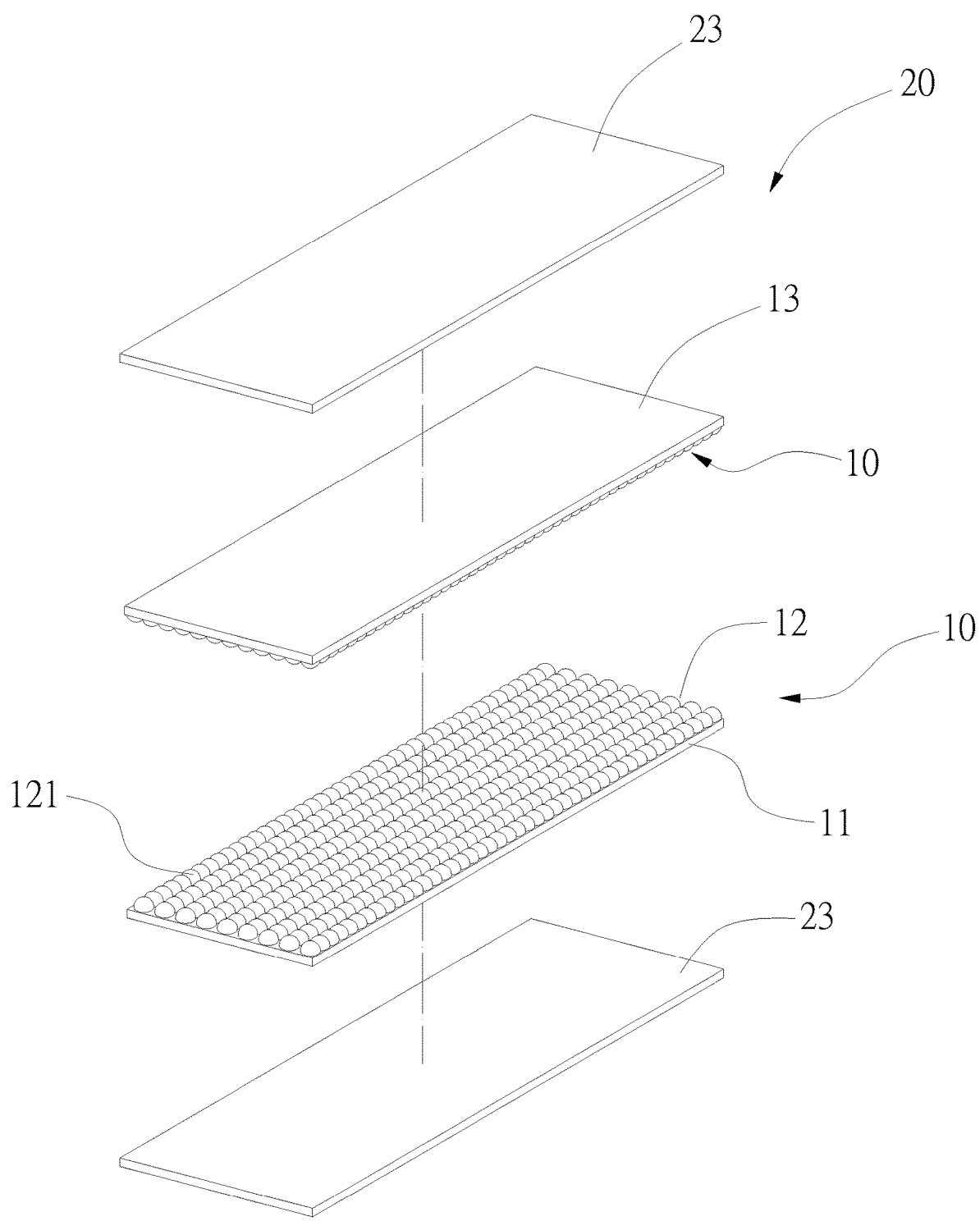
FIG. 11 is an explosive diagram showing a moistureproof patch being applied to a package the present disclosure.
Figure 12:
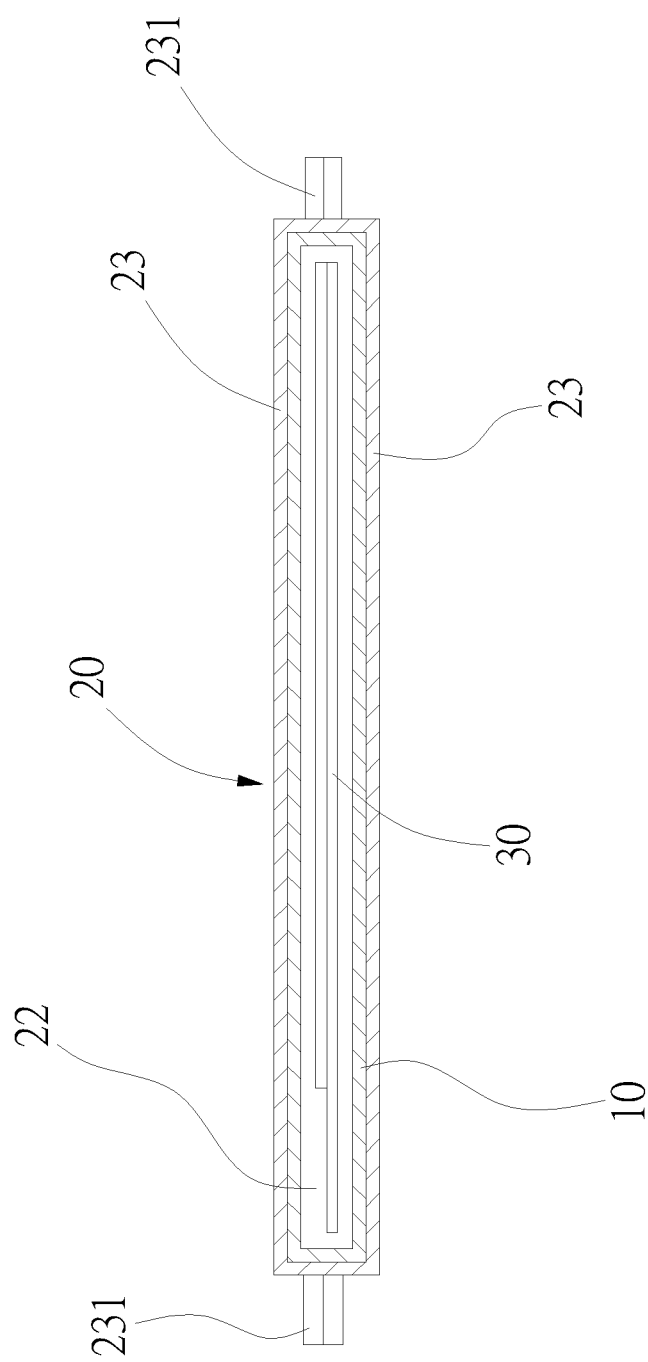
FIG. 12 is a sectional diagram showing a moistureproof patch being applied to another package the present disclosure.

Moreover, referring to FIG. 11 and FIG. 12, the container body 20 is formed by jointing the two packaging sheets 23, and specifically, the two packaging sheets 23 are stacked up and down. A periphery of the packaging sheets 23 has a thermocompression part 231 surrounding the periphery of the packaging sheets 23. The room 21 being closed is formed between the packaging sheets 23 and the thermocompression part 231. The biochemical test strip 30 is accommodated in an interior of the room 21. A side of the carrier 11 has an adhesion layer 13 being adhered to the packaging sheets 23, another side of the carrier 11 has the moistureproof layer 12 disposed in the room 21.

To further illustrate features of structures, utilized means and expected and achieved results of the present disclosure, the utilization of the present disclosure are described as follows. It is believed that the person with the ordinary skill in the art can understand the details of the present disclosure based upon the descriptions of the present disclosure.

Referring to FIG. 8 through FIG. 10, when the biochemical test strip 30 is disposed in the room 21, the moistureproof units 10 on the periphery of the room 21 can generate the moisture absorption effect. Since the moistureproof units 10 are adhered to the side wall 211, regardless that moisture is located at the position which the room 21 is neighboring to the opening 22 or the bottom wall 212, the moistureproof units 10 still have the great moisture absorption effect. In addition, since the semicircular water absorption units 121 are distributed on the whole moistureproof layer 12 of the moistureproof unit 10, the maximum moisture absorption area is used for absorbing the moisture, and the moisture absorption effect is enhanced. Further, since the moistureproof units 10 are adhered before accommodating the biochemical test strip 30, the moisture absorption performed before accommodating the biochemical test strip 30 is prevented, and the utilization efficiency can be increased.

Moreover, referring to FIG. 11 and FIG. 12, the biochemical test strip 30 is surrounded by the packaging sheets 23, so as to have a great sealing effect. Incorporated with the inner moistureproof units 10, even when the thermocompression part 231 has a gap via which the moisture can enter, the moistureproof units 10 can still have efficient moisture absorption effect, so as to ensure the effect of the biochemical test strip 30.

To sum up, the moistureproof unit and moistureproof container structure for accommodating the biochemical test strip provided by the present disclosure have not been anticipated by publications or used in public, which meet patentability of the invention. Examination of the present disclosure is respectfully requested, as well as allowance of the present disclosure.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A moistureproof container structure for accommodating at least one biochemical test strip, at least comprising:
    a moistureproof unit, being manufactured by using a method for manufacturing the moistureproof unit, wherein the method for manufacturing the moistureproof unit is comprising: preparing a sheet-shaped carrier; coating a moistureproof layer on said carrier by uniformly distributing a hydrophilic polymer material on a surface of said carrier, and depositing a plurality of semicircular water absorption units on the surface of the carrier in said hydrophilic polymer material; wherein a height of each of said plurality of semicircular water absorption units ranges between 0.2 mm and 0.6 mm, a diameter of said each water absorption unit ranges between 0.3 mm and 1.2 mm, a grain weight of said each water absorption unit ranges between 0.011 g and 0.013 g, and a distance between two neighboring of said plurality of semicircular water absorption units ranges between 0.17 mm and 0.57 mm;
    a container body, having a room, wherein the moistureproof unit is fixed in the room.

2. The moistureproof container structure for accommodating the at least one biochemical test strip according to claim 1, wherein one side of the room of the container body has an opening, a periphery of the room has a side wall surrounding the periphery of the room, and a bottom of the room has a bottom wall, the at least one biochemical test strip is accommodated in an interior of the room, wherein a top of the container body further has a cover body being configured to cover the opening.

3. The moistureproof container structure for accommodating the at least one biochemical test strip according to claim 1, wherein another side of the moistureproof layer of the moistureproof unit has an adhesion layer being adhered to the side wall of the room.

4. The moistureproof container structure for accommodating the at least one biochemical test strip according to claim 1, wherein a side the moistureproof unit is coated with an adhesion layer, and the moistureproof unit is spirally adhered to the cover body via the side of the moistureproof unit.

5. The moistureproof container structure for accommodating the at least one biochemical test strip according to claim 1, wherein the container body is formed by jointing at least one packaging sheet, a periphery of the packaging sheet has a thermocompression part surrounding the periphery of the packaging sheet, the room being closed is formed between the packaging sheet and the thermocompression part, and the at least one biochemical test strip is accommodated in an interior of the room;
    wherein a side of the carrier has an adhesion layer being adhered to the packaging sheet, another side of the carrier has the moistureproof layer, and the moistureproof unit is disposed in the room.

6. The moistureproof container structure for accommodating the at least one biochemical test strip according to claim 2, wherein the at least one biochemical test strip is selected from one of a blood glucose test strip, a uric acid test strip, a urine test strip, a lactic acid test strip and a cholesterol test strip.

7. The moistureproof container structure for accommodating the at least one biochemical test strip according to claim 5, the at least one biochemical test strip is selected from one of a blood glucose test strip, a uric acid test strip, a urine test strip, a lactic acid test strip and a cholesterol test strip.

8. The moistureproof container structure for accommodating the at least one biochemical test strip according to claim 1, wherein coating the moistureproof layer is processed by a spraying manner.

9. The moistureproof container structure for accommodating the at least one biochemical test strip according to claim 1, wherein coating the moistureproof layer is processed by a dispensing manner.

10. The moistureproof container structure for accommodating the at least one biochemical test strip according to claim 1, wherein material of the semicircular water absorption units is light-hardening resin with a viscosity being 16000 through 24000 CPS, a specific weight being 1.1 and a PH value being 1.21, wherein each of the plurality of semicircular water absorption units formed by using a dispensation of a piezoelectric nozzle has a height being 0.3 mm, a diameter being 0.6 mm and a grain weight being 0.012 g, and a distance between the two neighboring of said plurality of semicircular water absorption units is 0.37 mm.

11. The moistureproof container structure for accommodating the at least one biochemical test strip according to claim 2, wherein one side of the cover body has a connection rib being coupled to the container body.

\* \* \* \* \*